United States Patent
Capron et al.

(10) Patent No.: US 9,745,243 B2
(45) Date of Patent: Aug. 29, 2017

(54) SUPPORTED METAL CATALYST AND USE THEREOF FOR SELECTIVE OXIDATION OF GLYCEROL

(71) Applicants: PIVERT, Venette (FR); CENTRE NATIONAL DE LA RECHERCHE SCIENTIQUE (CNRS), Paris (FR); UNIVERSITÉ DES SCIENCES ET TECHNOLOGIES DE LILLE 1, Villeneuve d'Ascq (FR)

(72) Inventors: Mickaeel Capron, Bachy (FR); Franck Dumeignil, Fretin (FR); Elzbieta Skrzynska, Cracow (PL)

(73) Assignees: PIVERT, Venette (FR); CENTRE NATIONAL DE LA RECHERCHE SCIENTIFIQUE (CNRS), Paris (FR); UNIVERSITÉ DES SCIENCES ET TECHNOLOGIES DE LILLE 1, Villeneuve d'Ascq (FR)

( * ) Notice: Subject to any disclaimer, the term of this patent is extended or adjusted under 35 U.S.C. 154(b) by 0 days.

(21) Appl. No.: 15/027,395

(22) PCT Filed: Oct. 14, 2014

(86) PCT No.: PCT/FR2014/052612
§ 371 (c)(1),
(2) Date: Apr. 5, 2016

(87) PCT Pub. No.: WO2015/055942
PCT Pub. Date: Apr. 23, 2015

(65) Prior Publication Data
US 2016/0272565 A1    Sep. 22, 2016

(30) Foreign Application Priority Data

Oct. 15, 2013  (FR) .................................. 13 60029

(51) Int. Cl.
*C07C 51/235*  (2006.01)
(52) U.S. Cl.
CPC .................. *C07C 51/235* (2013.01)
(58) Field of Classification Search
None
See application file for complete search history.

(56) References Cited

U.S. PATENT DOCUMENTS 9,475,742 B2    10/2016  Pinel et al.
2012/0253067 A1 10/2012  Chaudhari et al.

FOREIGN PATENT DOCUMENTS

| CN | 101225041 A | 7/2008 |
|---|---|---|
| CN | 101695657 A | 4/2010 |
| EP | 201957 A2 | 11/1986 |
| EP | 2332899 A1 | 6/2011 |
| LV | 14079 B | 5/2010 |

OTHER PUBLICATIONS

Chornaja et al. Reac Kinet Mech Cat (2013) 108:341-357.*
International Preliminary Report on Patentability for PCT/FR2014/052612 filed Oct. 14, 2014. Mail Date: Apr. 19, 2016. 19 pages. (French original + English Translation).
Dan Liang et al. "Bimetallic Pt Cu catalysts for glycerol oxidation with oxygen in a base-free aqueous solution", Catalysis Communications, Elsevier Science, vol. 12, No. 12, Mar. 14, 2011 p. 1059-1062.
Bianchi C L et al. "Selective oxidation of glycerol with oxygen using mono and bimetallic catalysts based on Au, Pd and Pt metals", Catalysis Today, Elsevier Science, vol. 102-103, May 15, 2005. p. 203-212.
Elina Sproge et al. "Selective liquid phase oxidation of glycerol to glyceric acid over novel supported Pt catalysts", Journal of the Serbian Chemical Society vol. 78 No. 9 Jan. 1, 2013. p. 1359-1372.
Garcia et al. "Chemoselective catalytic oxidation of glycerol with air on platinum metals", Applied Catalysis Al General, Elsevier Science, vol. 127 No. 1-2, Jun. 22, 1995 p. 165-176.
Kimura H et al. "Selective oxidation of glycerol in a platinum-bismuth catalyst", Applied Catalysis A: General, Elsevier Science, vol. 96, No. 2, Mar. 26, 1993, p. 217-228.
N. Worz et al.: "Platinum-Bismuth-Catalyzed Oxidation of Glycerol: Kinetics and the Origin of Selective Deactivation", Journal of Physical Chemistry C, vol. 114 No. 2, Jan. 21, 2010. p. 1164-1172.
International Search Report issued for International Application No. PCT/FR2014/052612 filed Oct. 14, 2014 (13 Pages). Report completed Apr. 1, 2015, report mailed Apr. 15, 2015.
Dam et al. "Tuning selectivity of Pt/CaCO3 in glycerol hydrogenolysis A Design of Experiments approach" Catalysis Communications, Elsevier Science, Amsterdam, NL, vol. 13, No. 1, Jun. 6, 2011, pp. 1-5, XP028257030.
Korovchenko et al. "Oxidation of primary alcohols with air on carbon-supported platinum catalysts for the synthesis of aldehydes or acids" Catalysis Today, 121 (2007) 13-21.

(Continued)

*Primary Examiner* — Clinton Brooks
(74) *Attorney, Agent, or Firm* — Steinfl + Bruno LLP (57) ABSTRACT

A method for oxidation of glycerol into glyceric acid is described, which includes a step of treating glycerol with a supported metal catalyst in the presence of oxygen, said catalyst including platinum and a metal element selected from the group comprising tin, molybdenum, bismuth and a mixture thereof.

20 Claims, 4 Drawing Sheets

(56) References Cited

OTHER PUBLICATIONS

Kusunoki et al. "Highly active metal-acid bifunctional catalyst system for hydrogenolysis of glycerol under mild reaction conditions" Catalysis Communications 6 (2005) 645-649.

Montassier et al. "Transformation de polyols par catalyse hétérogène en phase liquid sur les métaux" Bulletin De La Société Chimique De France. 1989,No. 2, 148-155.

International Search Report for PCT/IB2013/060679 filed Dec. 5, 2013 on behalf of NOVANCE. Mail Date: Mar. 18, 2014. 7 pages. French original + English translation.

Written Opinion for PCT/IB2013/060679 filed Dec. 5, 2013 on behalf of NOVANCE. Mail Date: Mar. 18, 2014. 17 pages. French original + English translation.

Shen et al. "Efficient synthesis of lactic acid by aerobic oxidation of glycerol on Au—Pt/TiO2 catalysts" Chemistry—A European Journal, Wiley—V C H Verlag GMBH & Co. KGAA, Weinheim, DE, vol. 16, No. 25, Jan. 2010, pp. 7368-7371, XP009146561.

Non-Final Office Action for U.S. Appl. No. 14/653,156, filed Jun. 17, 2015 on behalf of Catherine Pinel. Mail Date: Dec. 30, 2015. 7 pages.

Notice of Allowance for U.S. Appl. No. 14/653,156, filed Jun. 17, 2015 on behalf of Catherine Pinel. Mail Date: Jun. 27, 2016. 7 pages.

\* cited by examiner

SUPPORTED METAL CATALYST AND USE THEREOF FOR SELECTIVE OXIDATION OF GLYCEROL

CROSS REFERENCE TO RELATED APPLICATIONS

The present application is the national stage entry of International Application No. PCT/FR2014/052612, filed on Oct. 14, 2014, which, in turn, claims priority to French Patent Application No. FR1360029, filed on Oct. 15, 2013.

TECHNICAL FIELD

The present invention relates to a supported catalyst comprising at least two metal elements (bimetal catalyst) and to its use in the selective oxidation of glycerol. The use of glycerol and in particular of biobased glycerol offers an alternative to the use of fossil resources, such as hydrocarbons.

PRIOR ART 2,3-Dihydroxypropanoic acid, commonly known as glyceric acid (GA), is the starting material for the synthesis of numerous chemical and cosmetic products. It plays an important role in particular in the pharmaceutical industry as metabolic accelerator of alcohols and also as treatment for liver diseases. GA can also be used in the synthesis of biopolymers.

The syntheses of glyceric acid from glycerol which are described in the literature are carried out at high temperatures, which increases not only the production costs but also the environmental impact of the synthesis. Furthermore, the use of unpurified glycerol has negative effects on the efficiency of the catalysts used to date.

DESCRIPTION OF THE INVENTION

It is thus an aim of the present invention to overcome one or more of these disadvantages, in particular by providing an alternative to the use of resources of fossil origin for the production of glyceric acid by the use of biobased glycerol and/or of unpurified glycerol.

Another object of the invention is to obtain, at mild temperatures, the synthesis of glyceric acid from glycerol with a good selectivity and/or a good conversion value.

The invention thus relates to a process for the specific oxidation of glycerol to give glyceric acid comprising a stage in which a supported bimetal catalyst, said catalyst comprising platinum and tin, is brought into contact with glycerol in the presence of oxygen.

The invention also relates to a process for the oxidation of glycerol to give glyceric acid comprising a stage in which glycerol and a supported metal catalyst are brought into contact in the presence of oxygen, said catalyst comprising platinum and a metal element chosen from the group consisting of tin, molybdenum, bismuth and a mixture of these. Preferably, the supported catalyst comprises platinum and just one other metal entity in combination with the platinum.

The invention is based on the surprising observation made by the inventors that the process according to the invention makes it possible to specifically orientate the oxidation of the glycerol to give glyceric acid ($CH_2OH$—$CHOH$—$COOH$) while very largely limiting the formation of glyceraldehyde and/or dihydroxyacetone.

Furthermore, the process according to the invention, as a result of the use of the abovementioned (bi)metal catalysts, makes it possible to drastically reduce the reaction temperature for the oxidation of glycerol to give glyceric acid.

According to the process of the invention, the oxygen can be added in the gas form, preferably under pressure (for example between 1 and 10 atmospheres) and preferably pure or as a mixture with other gases.

The invention also relates to the abovementioned process, in which the (bi)metal catalyst comprises platinum and tin, platinum and bismuth or platinum and molybdenum.

In addition, the catalyst of the process according to the invention can comprise:
platinum, tin and bismuth (trimetal catalyst),
platinum, tin and molybdenum (trimetal catalyst),
platinum, bismuth and molybdenum (trimetal catalyst), or
platinum, tin, bismuth and molybdenum (tetrametal catalyst).

It is preferable for the only metal entities present in the supported catalyst to be platinum, tin, molybdenum and bismuth. In this case, apart from the aluminum of the alumina supporting the catalyst, if other metal entities are present, they are present in the form of traces.

Advantageously, the invention relates to a process as defined above in which the stage of bringing into contact is carried out in the presence of base.

The term "base" denotes a compound capable of capturing one or more protons and vice versa of giving up one or more electrons. In the context of the invention, the term "base" most particularly denotes compounds such as sodium hydroxide or alkoxylated alkali metal salts, such as EtONa, MeONa or tBuOK, alone or as mixtures.

In another advantageous embodiment, the invention relates to a process as defined above in which the stage of bringing into contact is carried out at a temperature of less than or equal to 120° C., preferably of less than or equal to 100° C., Furthermore, this temperature can advantageously be chosen within the range extending from 15° C. to 100° C., particularly from 20° C. to 60° C. and more particularly from 28° C. to 60° C.

Another advantageous embodiment of the invention relates to a process according to the preceding definition in which the metal catalyst comprises tin and platinum, The relative proportion of the second metal with respect to the platinum can be chosen within a range extending from 1 to 30, preferably from 5 to 20 and more particularly from 8 to 12 (for example, the Sn/Pt. Mo/Pt or Bi/Pt ratio can be chosen in the vicinity of 10), by weight of these elements.

According to a specific aspect of the invention, the catalyst is supported by alumina. Thus, a particularly advantageous catalyst for putting the process of the invention into practice is a catalyst comprising or consisting of platinum and tin, platinum and molybdenum or platinum and bismuth, on an alumina support. Such catalysts according to the invention are described in the examples below.

Another advantageous embodiment of the invention relates to a process according to the above definition in which the base is sodium hydroxide.

Advantageously, the invention relates to a process as defined above in which the reaction products predominantly comprise glyceric acid and tartronic acid. Thus, according to another embodiment, the invention can relate to a process for the synthesis of tartronic acid.

This is because the process according to the invention makes it possible to obtain, as predominant products of the oxidation of glycerol: glyceric acid and, to a lesser extent, tartronic acid (HOOC—CHOH—COOH).

In yet another advantageous embodiment, the invention relates to a process as defined above, said process additionally comprising a stage of separation of the reaction products.

An example of a process for the separation of products from the oxidation reaction of glycerol according to the invention is presented in example 7 below.

According to a particularly advantageous aspect, the glycerol used is unrefined glycerol. Thus, the process according to the invention can be carried out with a composition based on glycerol but which also comprises other compounds or impurities. This is particularly advantageous as the process can exclude the need to purify or refine the glycerol, making it possible in particular to use biobased glycerol, or also to substantially reduce the level of purification required. Thus, glycerol comprising up to 50% by weight of impurities (crude glycerol) can be used as starting material.

According to another equally advantageous aspect of the process according to the invention, said supported catalyst can be recycled. In particular, the catalyst could have been subjected to a regeneration stage before being brought together with glycerol. Thus, the supported catalyst, if it loses its effectiveness during the synthesis process as a result of fouling and/or of impurities blocking the reaction sites during the oxidation reaction, can be separated from the reaction medium and treated in order to reestablish its effectiveness, at least partially. The catalysts according to the invention prove to be particularly suitable for being recycled (regenerated). This is because, once regenerated, they do not lose their effectiveness or lose only a very small amount of it.

The term "regeneration" is understood to mean, in the invention, the action of restoring its initial properties to the catalyst.

The regeneration treatment advantageously comprises a stage of washing, in particular with distilled water, and of drying, advantageously at more than 100° C. (for example, approximately 105° C.), for a sufficient period of time (for example, 24 hours).

The invention also relates to the use of a catalyst as defined above in the production of glyceric acid or tartronic acid from glycerol.

The invention also relates to a (bi)metal catalyst composed of 0.5 to 10% by weight of platinum and tin, molybdenum or bismuth, said catalyst being supported, and also to its use in the process according to the invention. The supported Pt/Sn. Pt/Mo and Pt/Bi catalysts, in particular supported by alumina, are covered by the invention, as are their process of manufacture and their use, in particular in the process according to the invention.

Advantageously, the invention relates to a (bi)metal catalyst composed of 0.5 to 10% by weight of platinum and of 1 to 30% by weight of tin, molybdenum or bismuth, said catalyst being supported, in particular supported by alumina.

According to a preferred embodiment, the invention also relates to a composition comprising glycerol, a supported catalyst as described above and abase.

According to another aspect of the invention, the invention also relates to the glyceric acid directly obtained by the process according to the invention.

A better understanding of the invention will be obtained on reading the figures and examples below, which are provided by way of illustration and do not exhibit any limiting nature.

EXAMPLES

Example 1

Synthesis of a Support Pt/Sn Bimetal Catalyst

The supported catalyst is prepared by incipient wetness impregnation of an alumina (15.7271 g) (Merck) with a solution of $SnCl_2 \cdot 2H_2O$ (5.3232 g) (Aldrich), followed by drying at 110° C. for 24 h and by calcination under air at 550° C. for 3 h, in order to obtain a support comprising 1.5 mmol of Sn per gram of alumina.

The support (Sn/alumina) (4.487 g) is immersed in water and brought to reflux for 30 min. 20.809 ml of an aqueous solution of $K_2PtCl_6$ salt (0.0164 mol.l$^{-1}$) are then added dropwise with strong stirring and reduced with $NaBH_4$ (2 mol.l$^{-1}$). After one hour of stirring and reflux, the solution is cooled to ambient temperature and filtered, and the filter residue is washed with water. Finally, the powder, comprising 1.4 wt % of Pt and 14.9 wt % of tin, is dried at 100° C. for 24 h before being used in the reaction for the oxidation of glycerol.

Example 2

Experimental Conditions

The same conditions were applied for all the catalytic tests presented in examples 3 to 6, namely: an oxygen pressure of 5 bar, a rotational speed of stirring of 1500 rpm, an initial glycerol concentration of 0.3M, an NaOH/glycerol ratio=4 or 0 and, finally, a glycerol/catalyst ratio=11 (g/g). The range of temperatures studied is between 28 and 100° C.

The experiments for the oxidation of pure glycerol in the liquid phase were carried out in a 300 ml stainless steel reactor equipped with a gas entrainment impeller, with four baffles, with a thermocouple and with a system for feeding with thermally regulated oxygen. In each experiment, 200 ml of an aqueous glycerol solution ([glycerol]=0.3M) are heated to the desired temperature and the reaction begins when the sodium hydroxide solution and/or the catalyst are introduced into the reactor (t0) and when the system is placed under oxygen pressure (5 bar) with continuous stirring (1500 rpm). The amount of base is adjusted in order to obtain an NaOH/glycerol molar ratio of between 0 and 4. The glycerol/catalyst weight ratio is 11. The temperature and the $O_2$ partial pressure are continuously monitored while the sampling is carried out periodically. The products are analyzed with an HPLC Agilent 1200 device equipped with a Rezex ROA-Organic Acid H+ column (300×7.8 mm) and a refractive index detector (RID). A solution of $H_2SO_4$ (0.0025M) in demineralized water (0.5 ml.min$^{-1}$) was used as eluent. The identification and the quantification of the products obtained are carried out by comparison with the corresponding calibration curves.

Example 3

Oxidation of Glycerol in the Presence of a Supported Pt/Sn Bimetal Catalyst at 100° C. in the Absence of Base The reaction is carried out under the conditions described in example 2 at a temperature of 100° C. and in the absence of base.

Figure 1:
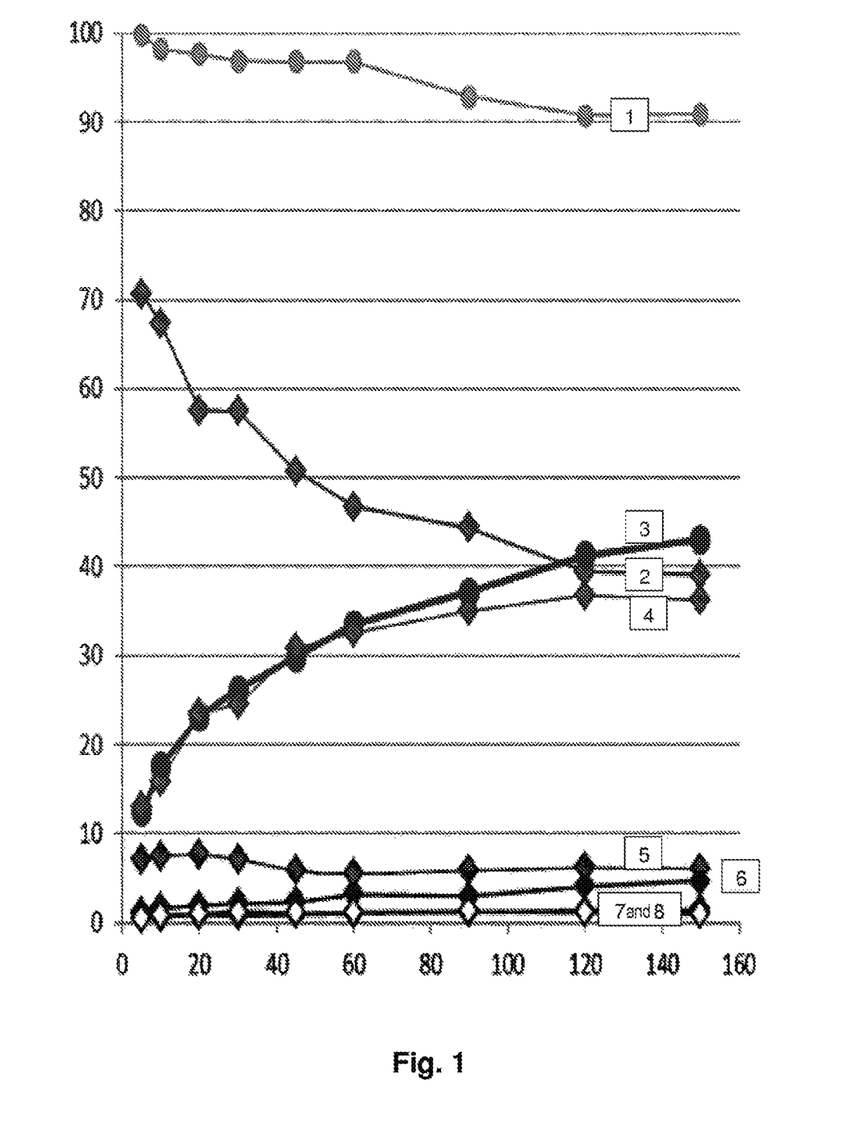
FIG. 1 represents a graph showing the percentage of products obtained over time in the context of the reaction for the oxidation of glycerol at 100° C. in the absence of base. The axis of the abscissae represents the time, expressed in minutes, and the axis of the ordinates represents the percentage of products. The key to FIG. 1 is as follows:
1: carbon balance
2: glyceraldehyde
3: degree of conversion of the glycerol [%]
4: glyceric acid
5: dihydroxyacetone (or 1,3-dihydroxy-2-propanone, or DHA)
6: glycolic acid
7: tartronic acid
8: oxalic acid

The results are represented in FIG. 1.

The conversion of glycerol reaches a maximum of 43.1% after 2.5 h of reaction. The predominant products are glyceraldehyde and glyceric acid, with respective yields of 16.8 and 15.6%.

Example 4

Oxidation of Glycerol in the Presence of a Supported Pt/Sn Bimetal Catalyst at 60° C. and in the Presence of Base The reaction is carried out under the conditions described in example 2 at a temperature of 60° C., in the presence of base.

Figure 2:
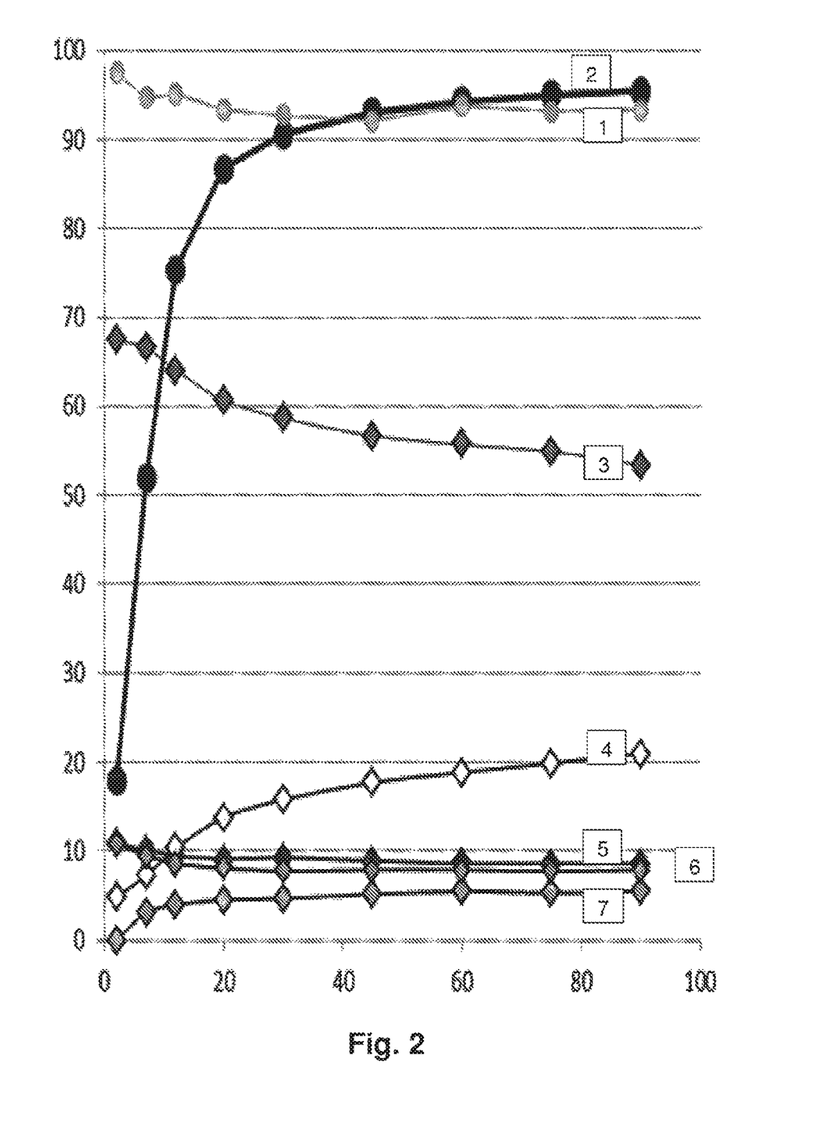
FIG. 2 represents a graph showing the percentage of products obtained over time in the context of the reaction for the oxidation of glycerol at 60° C. in the presence of base. The axis of the abscissae represents the time, expressed in minutes, and the axis of the ordinates represents the percentage of products. The key to FIG. 2 is as follows:
1: carbon balance
2: degree of conversion of the glycerol [%]
3: glyceric acid
4: tartronic acid
5: glycolic acid
6: formic acid
7: oxalic acid

The results are represented in FIG. 2.

The conversion of glycerol reaches 95% after 1.5 h of reaction. The predominant products are glyceric acid and tartronic acid, with respective yields of 50.9% and 20.0%.

Example 5

Oxidation of Glycerol in the Presence of a Supported Pt/Sn Bimetal Catalyst at 40° C. and in the Presence of Base The reaction is carried out under the conditions described in example 2 at a temperature of 40° C., in the presence of base.

Figure 3:
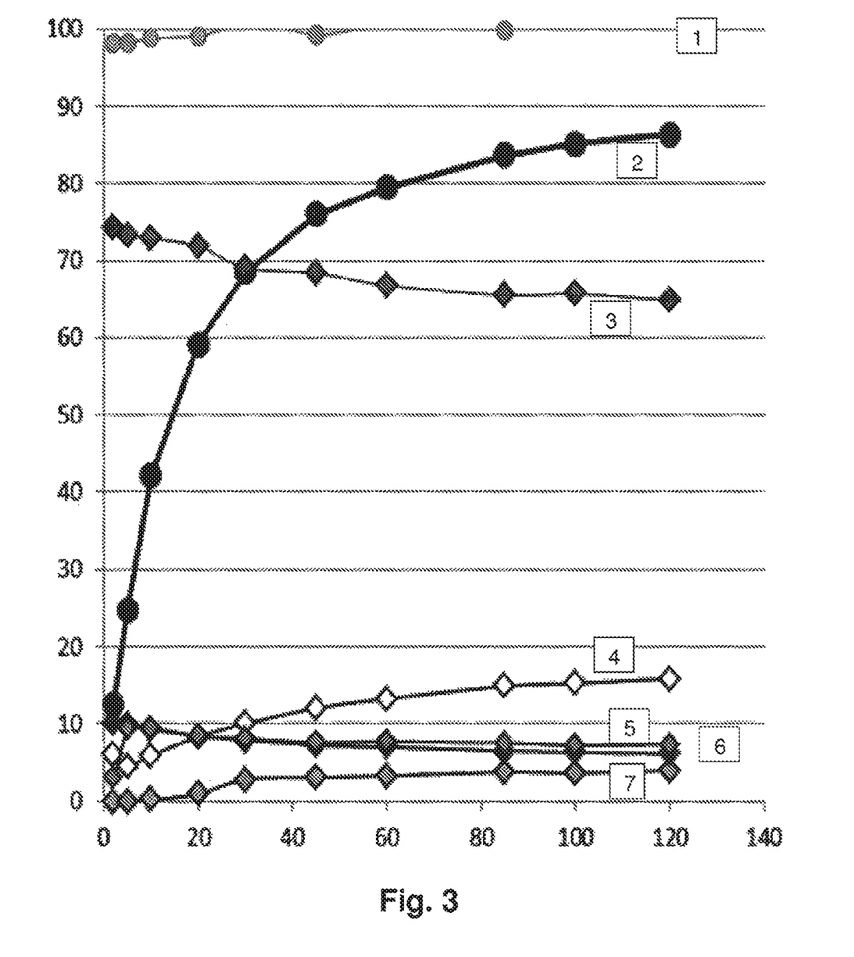
FIG. 3 represents a graph showing the percentage of products obtained over time in the context of the reaction for the oxidation of glycerol at 40° C. in the presence of base. The axis of the abscissae represents the time, expressed in minutes, and the axis of the ordinates represents the percentage of products. The key to FIG. 3 is as follows:
1: carbon balance
2: degree of conversion of the glycerol [%]
3: glyceric acid
4: tartronic acid
5: formic acid
6: glycolic acid
7: oxalic acid

The results are represented in FIG. 3.

The conversion of glycerol reaches 86.3% after 1.5 h of reaction. The predominant products are glyceric acid and tartronic acid with respective yields of 56% and 13.7%.

Example 6

Oxidation of Glycerol in the Presence of a Supported of a Pt/Sn Bimetal Catalyst at 28° C. and in the Presence of Base The reaction is carried out under the conditions described in example 2 at a temperature of 28° C., in the presence of base.

Figure 4:
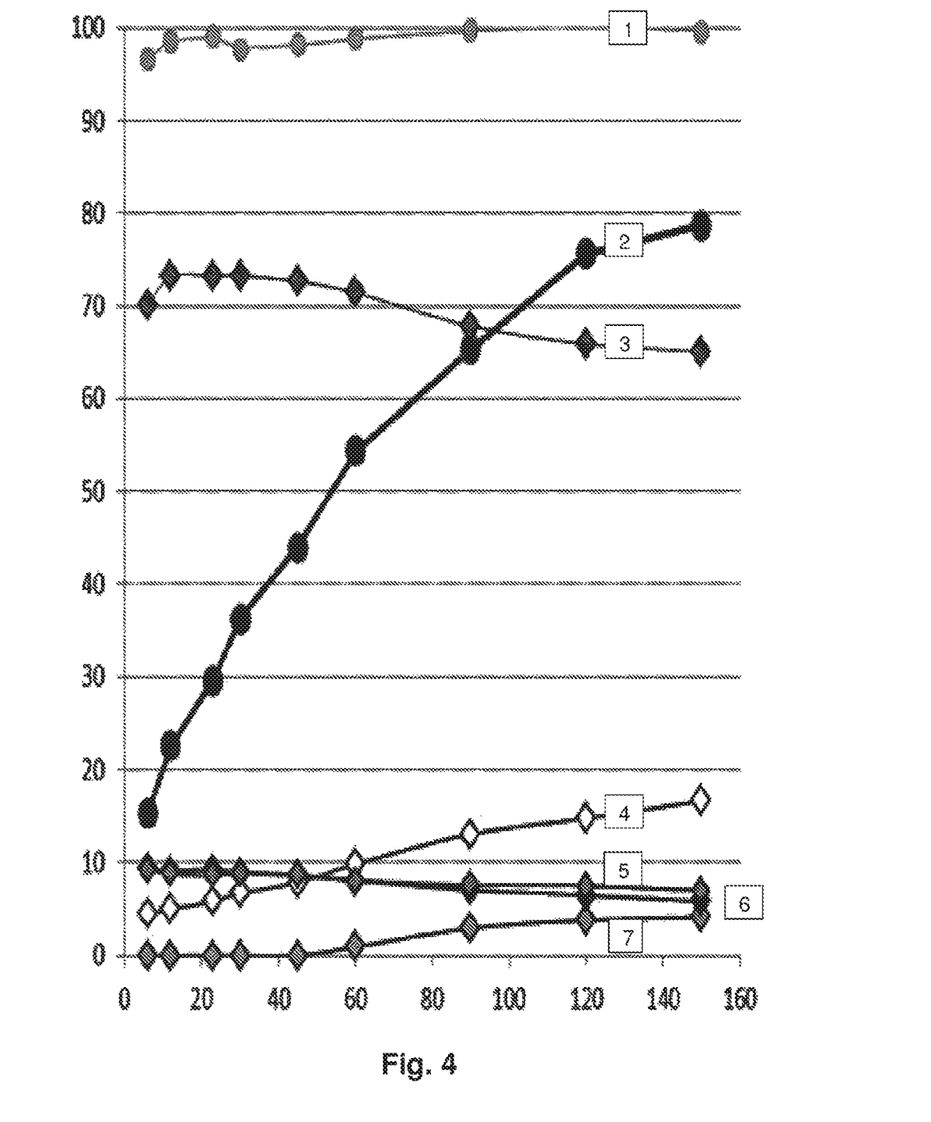
FIG. 4 represents a graph showing the percentage of products obtained over time in the context of the reaction for the oxidation of glycerol at 28° C. in the presence of base. The axis of the abscissae represents the time, expressed in minutes, and the axis of the ordinates represents the percentage of products. The key to FIG. 4 is as follows:
1: carbon balance
2: degree of conversion of the glycerol [%]
3: glyceric acid
4: tartronic acid
5: formic acid
6: glycolic acid
7: oxalic acid

The results are represented in FIG. 4.

The conversion of glycerol reaches 78.3% after 2.5 h of reaction. The predominant products are glyceric acid and tartronic acid with respective yields of 54.2% and 13.1%.

Example 7

Separation of the Reaction Products

In order to separate the reaction products (if the selectivity for glyceric acid does not reach 100%), it is sufficient to carry out a derivation by reaction with an alcohol (e.g. methanol or ethanol) in order to obtain the corresponding esters. These esters have a broad range of boiling points, thus making possible separation by fractional distillation. Reacidification of the different fractions subsequently makes it possible to obtain the different carboxylic acids.

The boiling points of the different esters obtained from the reaction of the acids with methanol are provided below. As may be seen, they are sufficiently separated to envisage different distillation stages.
  methyl glycerate=241.5° C.
  methyl glycolate=149-151° C.
  methyl oxalate=204° C. and 163-164° C. for the dimethyl ester
  methyl tartronate=316° C.
  methyl formate=32° C.

Other methods, such as membranes selective for $C_2$ compounds or adsorbents, can also be envisaged.

Example 8

Synthesis of the Supported Bimetal Catalyst PtBi/Al$_2$O$_3$

The supported catalyst is prepared by incipient wetness impregnation of an alumina (15.6664 g) (Merck) with a solution of $Bi(NO_3)_3.5H_2O$ (11.3989 g) (Avantor Performance Materials Poland S.A.), followed by drying at 110° C.

for 24 h and by calcination under air at 550° C. for 3 h, in order to obtain a support comprising 1.5 mmol of Bi per gram of alumina.

The support (Bi/alumina) (4.428 g) is immersed in water and brought to reflux for 30 min. 20.53 ml of an aqueous solution of $K_2PtCl_6$ salt (0.016 mol.l$^{-1}$) are then added dropwise with strong stirring and reduced with $NaBH_4$ (2 mol.l$^{-1}$). After one hour of stirring and of reflux, the solution is cooled to ambient temperature and filtered, and the filter residue is washed with water. Finally, the powder, comprising 1.46 wt % of Pt and 30.84 wt % of Bi, is dried at 100° C. for 24 h before being used in the reaction for the oxidation of glycerol.

Example 9

Synthesis of the Supported Bimetal Catalyst PtMo/Al$_2$O$_3$

The supported catalyst is prepared by impregnation of an alumina (14.9976 g) (Merck) with a solution of $MoO_3$ (3.2381 g) (Avantor Performance Materials Poland S.A.): the solution of $MoO_3$ is prepared beforehand by solubilization of $MoO_3$ in a solution of water at boiling point and at reflux, in the presence of a few drops of nitric acid (the water is used in excess until complete solubilization of $MoO_3$); then the alumina is added to this solution, under hot conditions, with stirring; after homogenization, the water is evaporated. The solid obtained is subsequently dried at 110° C. for 24 h and then calcined under air at 550° C. for 3 h, in order to obtain a support comprising 1.5 mmol of Mo per gram of alumina.

The support (Mo/alumina) (4.430 g) is immersed in water and brought to reflux for 30 min. 20.55 ml of an aqueous solution of $K_2PtCl_6$ salt (0.016 mol.l$^{-1}$) are then added dropwise with strong stirring and reduced with $NaBH_4$ (2 mol.l$^{-1}$). After one hour of stirring and of reflux, the solution is cooled to ambient temperature and filtered, and the filter residue is washed with water. Finally, the powder, comprising 1.46 wt % of Pt and 14.2 wt % of Mo, is dried at 100° C. for 24 h before being used in the reaction for the oxidation of glycerol.

Example 10

Study of Recyclability Carried Out on the Catalysts

Tests:

A preliminary study on recycling the catalysts is carried out by following the procedure described in example 2, with the following conditions: an oxygen pressure of 3 bar, a stirrer rotational speed of 1500 rpm, an initial glycerol concentration of 0.3M, a temperature of 60° C., an NaOH/glycerol ratio=4 and a glycerol/catalyst ratio=11 (g/g), The commercial catalyst Pt/Al$_2$O$_3$ is used for comparison.

Recycling Procedure:

After a first reaction carried out essentially under the conditions described in example 2, the catalyst is separated from the reaction medium by filtration, then washed with 200 ml of distilled water and dried at 105° C. for 24 hours. The catalyst is subsequently reused directly for a second reaction carried out under the same conditions as the first, without addition of fresh catalyst. The recycling procedure is repeated between each following reaction.

|  | 1$^{st}$ test | 2$^{nd}$ test | 3$^{rd}$ test |
|---|---|---|---|
| Pt/Al$_2$O$_3$ (Aldrich) | 82.1% conv. 30 min | 86 4% conv. 30 min | 85.3% conv. 30 min |
| Pt—Sn/Al$_2$O$_3$ | 95.4% conv. 30 min | 92.4% conv. 30 min | 81.9% conv. 30 min |
| Pt—Bi/Al$_2$O$_3$ | 95.9% conv. 30 min | 97.3% conv. 30 min | 97.9% conv. 30 min |
| Pt—Mo/Al$_2$O$_3$ | 99.9% conv. 30 min | 98.2% conv. 30 min | 99.0% conv. 30 min | conv. = "degree of conversion at"

The level of conversion remains constant for the bimetal catalysts Pt—Bi/Al$_2$O$_3$ and Pt—Mo/Al$_2$O$_3$. There is no loss of selectivity for glyceric acid, which remains constant (approximately 60% for the commercial catalyst, 65-75% for the bimetal catalysts).

Example 11

Oxidation of Unpurified Glycerol in the Presence of a Supported Pt/Sn Bimetal Catalyst at 60° C. and in the Presence of a Base The reaction is carried out at 60° C. under the conditions described in example 2 using crude glycerol (purity of approximately 50%). The commercial catalyst Pt/Al$_2$O$_3$ is used for comparison.

|  | Conversion (1 h) |
|---|---|
| Pt/Al$_2$O$_3$ (Aldrich) | 9.0% |
| Pt—Sn/Al$_2$O$_3$ | 32.3% |

The conversion of the glycerol reaches 9.0% with the commercial catalyst Pt/Al$_2$O$_3$, after 1 h of reaction, and 32.3% with the catalyst Pt—Sn/Al$_2$O$_3$. Compared with the reactions starting from pure glycerol, the activity of the commercial catalyst Pt/Al$_2$O$_3$ decreases by a factor of 5 with the unpurified glycerol. This loss is by a factor of 3 with the Pt—Sn/Al$_2$O$_3$ bimetal catalyst. The predominant products are glyceric acid and tartronic acid, with similar yields to those obtained from the crude glycerol.

The invention is not limited to the embodiments presented and other embodiments will be clearly apparent to a person skilled in the art.

The invention claimed is:

1. A process for oxidation of glycerol to glyceric acid, the process comprising contacting glycerol with a metal catalyst in presence of oxygen, wherein the metal catalyst is supported by alumina, said metal catalyst comprising platinum and a metal element chosen from the group consisting of tin, molybdenum, and a mixture thereof.

2. The process as claimed in claim 1, wherein the contacting is carried out in the presence of a base.

3. The process as claimed in claim 2, wherein the base comprises sodium hydroxide.

4. The process as claimed in claim 2, wherein the base consists of sodium hydroxide.

5. The process as claimed in claim 1, wherein the contacting is carried out at a temperature from 15° C. to 100° C.

6. The process as claimed in claim 5, wherein the temperature is from 20° C. to 60° C.

7. The process as claimed in claim 5, wherein the temperature is from 28° C. to 60° C.

8. The process as claimed in claim 1, wherein the metal catalyst comprises tin and platinum.

9. The process as claimed in claim 1, wherein the glycerol is unrefined glycerol.

10. The process as claimed in claim 1, wherein the contacting results in reaction products, wherein the products are predominantly glyceric acid and tartronic acid in yield percentage.

11. The process as claimed in claim 10, further comprising separating glyceric acid and tartronic acid.

12. The process as claimed in claim 1, further comprising separating reaction products resulting from the contacting.

13. The process as claimed in claim 1, further comprising regenerating said catalyst before the contacting a regenerated supported metal catalyst with glycerol.

14. The process as claimed in claim 13, wherein said regenerating comprises washing and drying the catalyst.

15. The process as claimed in claim 14 wherein the drying comprises heating at 105° C. for 24 hours.

16. A process for oxidation of glycerol to glyceric acid, the process comprising contacting glycerol with a supported metal catalyst in presence of oxygen, wherein the metal catalyst comprises molybdenum and platinum.

17. The process as claimed in claim 16, wherein the metal catalyst further comprises tin.

18. The process as claimed in claim 16, wherein the contacting is carried out in the presence of a base.

19. The process as claimed in claim 16, wherein the glycerol is unrefined glycerol.

20. The process as claimed in claim 16, further comprising regenerating said catalyst before the contacting a regenerated supported metal catalyst with glycerol.

* * * * *